United States Patent [19]
Johnson, Jr.

[11] Patent Number: 4,855,241
[45] Date of Patent: Aug. 8, 1989

[54] TUMOR DIAGNOSTIC METHOD

[75] Inventor: Eugene M. Johnson, Jr., St. Louis, Mo.

[73] Assignee: Washington University, Mo.

[21] Appl. No.: 198,948

[22] Filed: May 26, 1988

[51] Int. Cl.$^4$ .................. G01N 33/53; G01N 33/567; G01N 33/539
[52] U.S. Cl. ..................... 436/548; 436/503; 436/504; 436/539; 436/804; 436/813
[58] Field of Search ............... 436/503, 504, 539, 548, 436/547, 804, 813, 63, 64

[56] References Cited

U.S. PATENT DOCUMENTS 4,707,443  11/1987  Nelson et al. ..................... 435/7

FOREIGN PATENT DOCUMENTS 202005  11/1986  European Pat. Off.

OTHER PUBLICATIONS

Levi-Montalcini, Science 237, 1154–66 (1987).
Fabricant et al., Proc. Natl. Acad. Sci. U.S.A. 74(2), 565–569 (1977).
Ross et al., Proc. Natl. Acad. Sci. U.S.A. 81, 6681–85 (1984).
DiStephano and Johnson, Proc. Natl. Acad. Sci. U.S.A. 85, 270–274 (1988).
Grob et al., Proc. Natl. Acad. Sci. U.S.A. 80, 6819–23 (1983).
Taniuchi et al., Proc. Natl. Acad. Sci. U.S.A. 83, 4094–98 (1986).
Chandler et al., J. Biol. Chem. 259(11), 6882–89 (1984).
Yan and Johnson, Devel. Biol. 121, 139–148 (1987).

Primary Examiner—Robert J. Warden
Assistant Examiner—Eric Vacchio
Attorney, Agent, or Firm—Scott J. Meyer; James W. Williams, Jr.

[57] ABSTRACT

An in vitro diagnostic method for determining the presence of nerve growth factor receptor bearing tumors is disclosed which comprises determining the presence of an elevated level of a truncated nerve growth factor receptor in a sample of a body fluid from a patient afflicted with such tumor.

7 Claims, 2 Drawing Sheets

TUMOR DIAGNOSTIC METHOD

BACKGROUND OF THE INVENTION

This invention relates to a medical diagnostic method and, more particularly, to an in vitro diagnostic method for determining the presence of nerve growth factor receptor bearing tumors.

The presence of specific soluble proteins in human serum or urine has been useful in the detection and diagnosis of a variety of tumor and disease states and in measuring the efficacy of medico-surgical management of these conditions. Among these soluble factors are Bence Jones proteins in patients with multiple myeloma, carcinoembryonic antigen (CEA), and epidermal growth factor in patients with small cell and epidermoid carcinoma of the lung, medullary thyroid carcinoma, as well as carcinomas of the stomach and esophagus. Recently, another such protein, interleukin 2 receptor (IL-2R), has gained considerable attention as a potential marker for various autoimmune disorders such as systemic lupus erythematosus (SLE), rheumatoid arthritis, gout, bacterial endocarditis, type I insulin dependent diabetes, and active chronic autoimmune hepatitis, as well as a potential marker for T- and B-cell leukemia.

The implication of nerve growth factor (NGF) or its receptor (NGFR) in neoplasia in the central and peripheral nervous system has been considered for a number of years. See, e.g., R. Levi-Montalcini, *Science* 237, 1154–1166(1987), for a review of the history of NGF research. As a result, determination of the presence of NGFR in human cells and tissue has been proposed as a means of diagnosis for certain tumors. Thus, Fabricant et al., *Proc. Natl. Acad. Sci. U.S.A.* 74(2), 565–569 (1977), describe the presence of NGFR on human melanoma cells (A875) in culture. It was reported that purified mouse NGF (2.5S,β-subunit preparation) when radiolabeled with $^{125}$I was found to bind readily with the A875 melanoma cells.

More recently, Ross et al., *Proc. Natl. Acad. Sci. U.S.A.* 81, 6681–6685 (1984), characterized the NGFR in neural crest tumors using monoclonal antibodies. The monoclonal antibodies were prepared, for example, by using human melanoma cell line WM245 cells as the immunogen in mice for obtaining hybridoma cells to produce monoclonal antibody 20.4 (IgG). It was shown that the NGFR is expressed on melanoma cells in much greater quantities than on normal melanocytes.

In European Patent Application No. 202,005, published Nov. 20, 1986, a diagnostic method for the detection of neural crest tumors is disclosed which consists of contacting human cells with antibody that is specific for NGFR having an average molecular weight of about 75,000 daltons.

The foregoing methods for determining NGFR levels involve histochemical identification which necessitate the inconvenient invasive procedure of making a biopsy of the test tissue.

BRIEF DESCRIPTION OF THE INVENTION

In accordance with the present invention an in vitro diagnostic method is provided for determining the presence of a nerve growth factor receptor bearing tumor in a patient afflicted with such tumor. The method comprises determining the presence of an elevated level of a truncated nerve growth factor receptor (NGFRt) in a sample of body fluid from said patient. The diagnostic method is illustrated in detail hereinafter by a crosslink immunoprecipitation assay to detect and semi-quantitate NGFRt in urine. The immunoassay can also be carried out on other body fluids such as blood and cerebrospinal fluid A major utility of this diagnostic method lies in the initial non-invasive detection of such tumors. An important clinical use would be in monitoring the reduction in tumor burden of an already diagnosed and therapeutically treated individual. The biochemical assay comprises a convenient, non-invasive method of detecting patients coming out of remission.

Recently, the present inventor identified a truncated form of the nerve growth factor receptor (NGFRt) in amniotic fluid, neonatal urine and neonatal plasma of rats. The results are reported by DiStephano and Johnson, *Proc. Natl. Acad. Sci. U.S.A.* 85, 270–274 (1988). The presence of this 50 kilodalton protein was detected by immunoprecipitation with monoclonal antibody and analyzed by sodium dodecylsulfate polyacrylamide gel electrophoresis (SDS-PAGE) and subsequent autoradiography.

It has now been found in accordance with the present invention that determination of elevated levels of NGFRt in human body fluids can be used as an indicator of the presence of NGFR bearing tumors such as, for example, neuroblastoma, melanomas, chondrosarcoma, Schwannoma and Ewing's sarcoma.

DETAILED DESCRIPTION OF THE INVENTION

Figure 1:
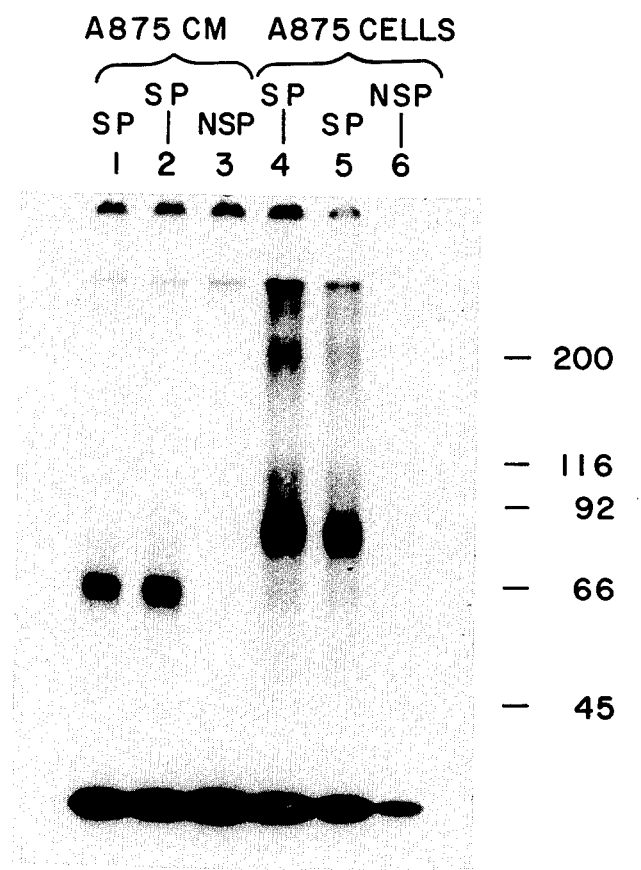

While the specification concludes with claims particularly pointing out and distinctly claiming the subject matter regarded as forming the present invention, it is believed that the invention will be better understood from the following detailed description of preferred embodiments taken in connection with the accompanying drawings in which, briefly:

FIG. 1 shows an autoradiogram of NGFR or NGFRt crosslinked to $^{125}$I-NGF and immunoprecipitated with anti-NGFR monoclonal antibody (MAb 20.4). Lanes 1–3 are samples of conditioned medium (CM) of A875 melanoma cells showing a receptor species at ≈75 KDa. Lanes 4–6 are receptors solubilized from A875 cells indicating a species at 90 KDa. Lanes 3 and 6 are immunoprecipitates in the presence of 400–fold excess unlabeled NGF. SP=specific binding lanes; NSP=nonspecific binding lanes. Molecular weight standards in kilodaltons (KDa) are indicated on the right hand side in FIGS. 1 to 3.

Figure 2:
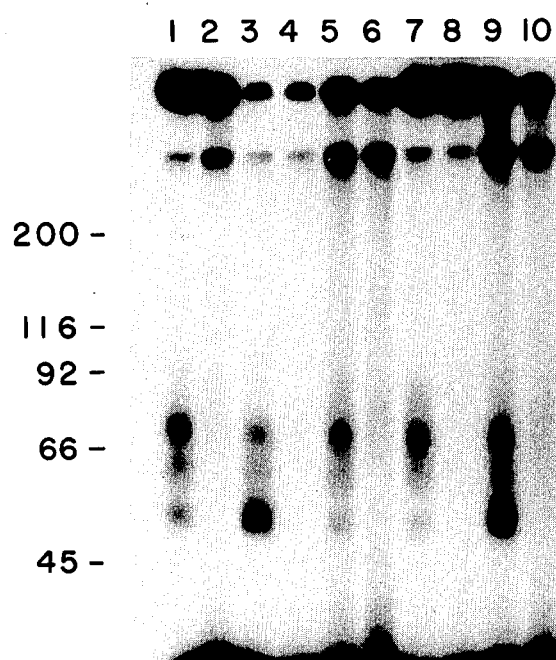

FIG. 2 shows an autoradiogram of NGFRt's immunoprecipitated from urine of five infants (lanes 1, 3, 5, 7, 9). Lanes 2, 4, 6, 8, 10 are immunoprecipitates in the presence of 400 -fold excess unlabeled NGF. Ages of infants are: 4 months for lanes 1, 2; newborn, lanes 3, 4; 7 months, lanes 5, 6; 1 day, lanes 7, 8; 1 week, lanes 9, 10.

Figure 3:
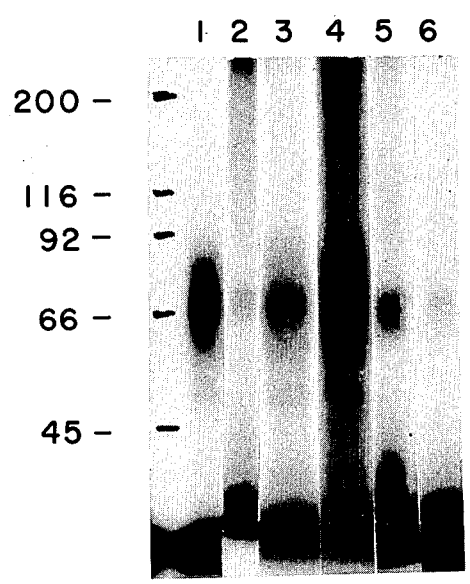

FIG. 3 shows an autoradiogram of NGFRt's immunoprecipitated from urine of patients with neuroblastoma (lane 1), Ewing's sarcoma (lane 2), Schwannoma (lane 3), chondrosarcoma (lane 4), melanoma (lanes 5, 6). Lane 5 is positive while 6 is negative for NGFRt. Determination of the presence of the truncated nerve growth factor receptor((NGFRt) is exemplified herein by a two-site crosslink immunoprecipitation assay. It is known that NGFR is a membrane-associated protein which, when $^{125}$I-NGF is chemically crosslinked to it, can be specifically immunoprecipitated with an appropriate antibody and visualized autoradiographically after sodium dodecyl sulfate polyacrylamide gel electrophoresis. This procedure typically yields labeled bands at ≈90-100 KDa and ≈220 KDa (potentially a dimer of the 90 KDa species). See Grob et al., *Proc. Natl. Acad. Sci. U.S.A.* 80, 6819–6823 (1983). The immunoprecipitation assay herein employs autoradiograms of NGFR and NGFRt cross-linked to $^{125}$I-NGF and immunoprecipitated with a human-specific anti-NGFR monoclonal antibody. The NGFRt is shown visually by labeled bands in SDS-PAGE gels in the range of about 50 to 70 kilodaltons.

The crosslink immunoprecipitation assay can be carried out by procedures substantially analogous to the immunoprecipitation assay for the full nerve growth factor receptor (NGFR) as described by Taniuchi et al., *Proc. Natl. Acad. Sci. U.S.A.* 83, 4094–4098 (1986). The illustrative assay herein thus employs the following steps:

(1) Prepare radioiodinated mouse NGF or $^{125}$I-NGF;

(2) Incubate the urine or other body fluid specimen containing the NGFRt with $^{125}$I-NGF and allow to bind;

(31) Crosslink the $^{125}$I-NGF to the bound receptor with 1-ethyl-3-(dimethylaminopropyl)carbodiimide (EDC);

(4) Immunoprecipitate the crosslinked receptor with anti-NGFR monoclonal antibody; and (5) Analyze the immunoprecipitate by sodium dodecylsulfate polyacrylamide gel electrophoresis and subsequent autoradiography.

Other immunoassay procedures can likewise be used in the diagnostic method of the invention, such as one- and two-site radioimmunoassays and enzyme immunoassays, for example, an enzyme-linked immunosorbent assay (ELISA) as described by Engvall and Perlmann, *J. Immunol.* 109, 129–135 (1972).

The monoclonal antibody production can be carried out by conventional hybridoma procedure such as described, for example, by Kohler and Milstein, *Nature* 256, 495–497 (1975); *Eur. J. Immunol.* 6, 1 511–519 (1976). According to this method, tissue-culture adapted mouse myeloma cells are fused to spleen cells from immunized mice to obtain the hybrid cells that produce large amounts of a single antibody molecule. A source of NGFR or NGFRt is used as the immunogen for producing the desired anti-NGFR activity in accordance with the present invention. A suitable mouse myeloma cell line is the well-known SP2/0-14 Ag cell line of BALB/c origin defined by Schulman et al., *Nature* 276, 269–70 (1978), the disclosure of which is incorporated herein by reference. Samples of these cells are available to the public from the American Type Culture Collection, Rockville, Md., under the accession number ATCC CRL-1581. A suitable method of carrying out the fusion of the myeloma cells and the immunized spleen cells is the conventional procedure described by Galfre et al.,

*Nature* 266, 550-2 (1977), whereby polyethylene glycol (PEG) is used as the fusing agent for the cells growing as monolayers. Cells can be cultured in HAT (hypoxanthine, aminopterin and thymidine) selection medium described by Littlefield, *Science* 145, 709 (1964).

The illustrative anti-NGFR monoclonal antibody 20.4 (IgG) used hereinafter was prepared by procedures substantially analogous to the method for preparing anti-NGFR 192 (IgG) by Chandler et al., *J. Biol. Chem.* 259 (11), 6882-6889 (1984), by using human melanoma cells instead of rat pheochromocytoma cell membranes as the immunogen. See Ross et al., supra. The 20.4 hybridoma also is available from the American Type Culture Collection, Rockville, Md., under accession number ATCC HB 8737.

Further background information on the preparation and use of monoclonal antibodies can be had by reference to a general text such as, for example, Goding, *Monoclonal Antibodies: Principles and Practice*, Academic Press Inc., New York 1983.

The following examples will illustrate the invention with greater detail although it will be appreciated that the invention is not limited to these specific Examples.

EXAMPLES

Materials and Methods

Cell Cultures. A875 melanoma cells were obtained from the laboratory of George J. Todaro (see Fabricant et al., supra) and grown in McCoy's 5a medium with 10% fetal calf serum (FCS). Two Ewing's cell lines, Esa-1 and RD-ES, purchased from ATCC, under accession numbers ATCC HTB 83 and ATCC HTB 166, respectively, were grown in McCoy's 5a medium with 25% FCS for the former and in RPMI 1640 with sodium pyruvate and 15% FCS for the latter. The neuroblastoma cell line NLB-127 was a kind gift from Dr. Milton Goldstein (Washington University School of Medicine) and was maintained on minimal essential medium with 1% nonessential amino acids and 20% FCS.

Amniotic Fluids and Urine Samples. Amniotic fluids were obtained from the amniocentesis center at Jewish Hospital of St. Louis. Normal infant urine samples were provided by the clinical chemistry laboratory at St. Louis Children's Hospital, and urines from patients with neuroblastoma or Ewing's sarcoma came from the hematology/oncology unit at St. Louis Children's Hospital. Melanoma patient urine was provided by Phillip Mustoe at Barnes Hospital, St. Louis, and urine of patients with Schwannomas or chondrosarcomas were obtained through Keith Rich at Barnes Hospital.

Immunoprecipitation Assays. NGF purified from male mouse submaxillary glands [Bocchini and Angeletti, *Proc. Natl. Acad. Sci. U.S.A.* 64 787–794 (1969)] was iodonated [Marchalonis, *Biochem. J.* 113, 299–305 (1969)] to a specific activity of 2000–3500 cpm/fmol. NGFR on cell surfaces was assayed by incubating cells washed in physiologic saline, with 2nM $^{125}$I-NGF in phosphate buffered saline (PBS) for 1 hr. Nonspecific sites were determined in the presence of 300–400 fold excess cold NGF. NGF was crosslinked to receptor species by incubating 20 min. with EDC [Taniuchi et al., *Proc. Natl. Acad. Sci. U.S.A.* 83, 1950–1954, 4094–4098 (1986)] and unreacted sites were quenched with addition of 50 mM Tris-HCl, pH 7.4. After washing the cells, they were solubilized in the presence of 1.3% n-octylglucoside for 1 hour. The sample was then spun on a Beckman microfuge at 12,000 x g for five minutes, and to the supernatant was added 5 μg anti-NGFR monoclonal antibody 20.4-IgG. After a one-hour incubation, 20 μ10% Pansorbin® suspension (Calbiochem) was added which previously had been saturated with anti-mouse IgG antibody. [Pansorbin cells are killed, hardened cells of *Staphylococcus aureus*, Cowan I strain, coated with immune-globulin-binding protein A on the cell surfaces.] After a one-hour incubation, the mixture was centrifuged and washed three times with PBS, 0.1% bovine serum albumin, 0.1%

Triton ® X-100, and 0.5M sucrose. A final wash in PBS-0.1% Triton X-100 followed. Soluble NGF receptor species in the truncated form were assayed similarly except the octylglucoside solubilization step with subsequent centrifugation was omitted.

The anti-NGFR monoclonal antibody was added directly to the sample with crosslinked NGF. The immunoprecipitates were resuspended in reducing SDS-PAGE sample buffer, boiled five minutes, and respun. Supernatants were chromatographed on a 7% polyacrylamide gel, dried, and visualized autoradiographically with Kodak X-Omat AR-5 film (Eastman Kodak, Rochester, N.Y.). NaI$^{125}$ was obtained from Amersham (Chicago, Ill.).

Results

The presence of a truncated form of the NGFR from a human-cell source was detected by $^{125}$I-NGF crosslink/immunoprecipitation assay with the monoclonal antibody 20.4 in media conditioned by A875 melanoma cells (FIG. 1). The cellular receptor complex has a mean molecular weight of 90 KDa. The molecular weight of soluble (NGFRt) component from the media is 75 KDa. Given that a monomer of NGF is 13 KDa, this yields apparent molecular weights of these NGF binding species as 77 KDa for the membrane-expressed receptor and 62 KDa for the soluble receptor.

In addition to the A875 cell system, the following cell lines were also shown to express $\approx 75$ KDa NGF-binding (weight includes NGF), 20.4-precipitable species in their conditioned growth medium: Ewing's lines Esa-1 and RD-Es, and the neuroblastoma NLB-127.

To compare with the results in rat [reported by DiStephano and Johnson, supra], amniotic fluid of human fetuses ranging in gestational age of 14–35 weeks contained three NGF binding proteins. These were specifically labeled and immunoprecipitated (data not shown). Urine obtained from five infants showed significant levels of the same bands seen in amniotic fluid (FIG. 2, lanes 1, 3, 5, 7, and 9) corresponding to proteins of apparent molecular masses of about 60, 45 and 35 KDa. With increasing postnatal age, the levels of these proteins declined to a point indistinguishable from background in normal adults.

The presence of elevated NGFRt levels was also detected by immunoprecipitation in the urine of some, but not all, patients bearing tumors of neural crest origin (FIG. 3). Positive tumors include neuroblastoma, Ewing's sarcoma, Schwannoma, chondrosarcoma, and melanoma. In all these cases, in contrast to results in amniotic fluids and infant urine specimens, the $\approx 70$ KDa band was consistently the strongest of the triad of species immunoprecipitated.

Various other examples will be apparent to the person skilled in the art after reading the present disclosure without departing from the spirit and scope of the invention. For example, similar immunoassays can be made on blood and cerebrospinal fluid specimens of patients having NGFR bearing tumors. So also, ELISA procedures can be used in place of the two-site radioimmunoassay with substantially similar results as in the foregoing examples. Polyclonal antibodies can be used instead of the monoclonal antibodies, although the latter are preferred in the diagnostic assay. It is intended that all such other examples be included within the scope of the appended claims.

What is claimed is:

1. An in vitro diagnostic method for determining the presence of a nerve growth factor receptor bearing tumor in a patient afflicted with such tumor comprising determining the presence of a truncated nerve growth factor receptor in a sample of a body fluid from said patient at a level which is elevated relative to the level in a normal patient.

2. The method of claim 1 in which the presence of the truncated nerve growth factor receptor is determined in a human urine sample by an immunoprecipitation assay with anti-nerve growth factor receptor antibodies.

3. The method of claim 2 in which the antibodies are monoclonal antibodies.

4. The method of claim 2 in which the immunoprecipitation assay results of the truncated nerve growth factor receptor are detected by autoradiography of radiolabeled bands in SDS-PAGE gels in the range of about 50 to 70 kilodaltons.

5. The method of claim 4 in which the urine sample is incubated with $^{125}$I-NGF and allowed to bind and in which the resulting bound receptor and the $^{125}$I-NGF are crosslinked with EDC.

6. The method of claim 1 in which the tumor is a neural crest tumor.

7. The method of claim 6 in which the neural crest tumor is selected from the group consisting of neuroblastoma, Ewing's sarcoma, Schwannoma, chondrosarcoma and melanoma.

* * * * *